(12) United States Patent
Wakikaido et al.

(10) Patent No.: US 7,588,570 B2
(45) Date of Patent: Sep. 15, 2009

(54) MEDICAL TREATMENT INSTRUMENT AND MEDICAL TREATMENT APPARATUS INCLUDING THE SAME

(75) Inventors: Koichi Wakikaido, Yao (JP); Tohru Tani, c/o Shiga University of Medical Science, Setatsukinowacho, Otsu-shi, Shiga (JP) 520-2192

(73) Assignee: Tohru Tani, Otsu-shi, Shiga (JP)

( * ) Notice: Subject to any disclaimer, the term of this patent is extended or adjusted under 35 U.S.C. 154(b) by 537 days.

(21) Appl. No.: 10/557,567

(22) PCT Filed: Jun. 7, 2004

(86) PCT No.: PCT/JP2004/008251

§ 371 (c)(1),
(2), (4) Date: Nov. 21, 2005

(87) PCT Pub. No.: WO2004/108001

PCT Pub. Date: Dec. 16, 2004

(65) Prior Publication Data

US 2007/0054539 A1    Mar. 8, 2007

(30) Foreign Application Priority Data

Jun. 9, 2003  (JP)  .............................. 2003-164338
Oct. 16, 2003 (JP)  .............................. 2003-356038

(51) Int. Cl.
*A61B 18/18* (2006.01)

(52) U.S. Cl. .......................................... 606/52; 606/45
(58) Field of Classification Search ................... 606/37, 606/39, 45, 48, 41, 51–52
See application file for complete search history.

(56) References Cited

U.S. PATENT DOCUMENTS

| 3,651,811 | A  |   | 3/1972  | Hilderbrandt et al. |
|-----------|----|---|---------|---------------------|
| 5,478,347 | A  | * | 12/1995 | Aranyi ............ 606/170 |
| 5,833,690 | A  | * | 11/1998 | Yates et al. ........ 606/52 |
| 6,267,761 | B1 | * | 7/2001  | Ryan ............... 606/50 |
| 6,387,094 | B1 | * | 5/2002  | Eitenmuller ........ 606/48 |

FOREIGN PATENT DOCUMENTS

| JP | 2001-61848  | 3/2001 |
| WO | WO 99/12487 | 3/1999 |
| WO | WO 01/12090 | 2/2001 |

* cited by examiner

*Primary Examiner*—Michael Peffley
*Assistant Examiner*—Samantha Muro
(74) *Attorney, Agent, or Firm*—Kilyk & Bowersox, P.L.L.C.

(57) ABSTRACT

A central electrode (12a) and an outer electrode (16a) are arranged in such a manner that their top end portions are inclined in the same direction with respect to the axial direction of the outer conductor (14). When the outer conductor (14) and the movable conductor (16) are relatively shifted in the axial direction, the central electrode (12a) and the outer electrode (16a) slidingly move on each other along the inclined direction, whereby a biotissue is cut between the central electrode (12a) and the outer electrode (16a).

10 Claims, 9 Drawing Sheets

MEDICAL TREATMENT INSTRUMENT AND MEDICAL TREATMENT APPARATUS INCLUDING THE SAME

This application is a National Stage Application of PCT/JP2004/008251, filed Jun. 7, 2004.

BACKGROUND OF THE INVENTION

1. Field of the Invention

The present invention relates to a medial treatment instrument configured so as to grip a biotissue as well as coagulate and cut the biotissue.

2. Description of the Related Art

Various medical treatment instruments for coagulating and cutting a biotissue have been conventionally known. For example, an apparatus for sealing and cutting a biotissue disclosed in the specification of U.S. Pat. No. 6,267,761 (hereinafter, referred to as prior art document) includes a pair of conductors arranged in parallel to each other, and each conductor includes at its end portion an electrode protruding in a direction perpendicular to the axial direction thereof. When the apparatus is used, the conductors are shifted in their axial directions to bring their electrodes close to each other, thereby gripping the biotissue between the electrodes. In this state, a coagulation high-frequency voltage is applied between the electrodes to generate thermal energy, and the biotissue is coagulated between the electrodes by use of thus-generated thermal energy.

However, the apparatus of the aforementioned prior art document for sealing and cutting a biotissue merely has a function of pinching the biotissue. When it is desired to cut the biotissue after coagulation, instead of applying a coagulation high-frequency voltage, it is required to apply between the electrodes a cutting high-frequency voltage (for example, a high-frequency voltage having a current waveform different from that of the coagulation high-frequency voltage) capable of generating thermal energy higher than the coagulation high-frequency voltage (see lines 49 to 50 in the second paragraph of the prior art document), and shift the electrodes toward each other at the same time. As described above, in order to coagulate and cut a biotissue by use of the sealing and cutting apparatus of the prior art document, the special electric power generator is required that generates a voltage for coagulation and a voltage for cutting respectively. This results in not only increased cost of the high-frequency power source but also large-sized high-frequency power source.

FIG. 7 in the prior art document discloses a structure in which the opposed surfaces of the electrodes are formed with recesses and projections engageable with each other. However, the apparatus of the prior art document cuts a biotissue only by use of the force applied in the direction of bringing the electrodes close to each other, that is, only by use of the force applied in the direction of gripping the biotissue. In this arrangement, even if the electrodes are formed with recesses and projections, the electrodes merely deform the biotissue into a thin form therebetween, and cannot cut the biotissue without utilizing the aforementioned cutting high-frequency voltage.

Further, if the recesses and projections are sharp-shaped to cut a biotissue, the surface of the biotissue is likely to be damaged when merely pinched by the electrodes. The biotissue damaged before coagulation is liable to bleed. This is not acceptable.

The present invention has been made in view of the problems described above, and an objective of the present invention is to provide a medical treatment instrument which can coagulate and cut a biotissue even only by use of a high-frequency power source only capable of generating a coagulation high-frequency voltage.

SUMMARY OF THE INVENTION

According to an aspect of the invention, a medical treatment instrument comprises a first conductor and a second conductor extending in parallel directions to each other and relatively shiftable in their axial directions, and a high-frequency voltage being applied to the top end portions of the conductors so as to coagulate and cut a biotissue held between a top end portion of the first conductor and a top end portion of the second conductor. The top end portion of the first conductor and the top end portion of the second conductor are inclined in the same direction with respect to the axial directions of the both conductors, and the relative shift of the conductors in their axial directions allows the top end portions of the both conductors to come close to each other to grip the biotissue therebetween, and the conductors are further relatively shifted in their axial directions to thereby shift the top end portions of the conductors relatively along the inclined directions with their top end portions gripping the biotissue, and slid against the biotissue in the same direction to cut the biotissue. These and other objects, features, aspects, and advantages of the present invention will become more apparent from the following detailed description of the preferred embodiments/examples with reference to the accompanying drawings.

BRIEF DESCRIPTION OF THE DRAWINGS

FIG. 3 is a sectional front view showing the shape of a central electrode 12a and an outer electrode 16a.

FIGS. 4 are partially enlarged side views showing states where the medical treatment instrument shown in FIG. 1 is used, wherein

FIGS. 5 are conceptual diagrams showing vectors of forces applied from the medical treatment instrument to a biotissue, wherein

FIGS. 6 are partially enlarged side views showing another use of the medical treatment instrument shown in FIG. 1, wherein

DETAILED DESCRIPTION OF THE PREFERRED EMBODIMENTS

Hereinafter, a preferred embodiment of the present invention will be described with reference to drawings by way of a high-frequency power source capable of supplying microwave electric power, which is an example of a high-frequency electric power. Here, the term "microwave" means an entire band of microwaves having a main frequency of 2.45 GHz.

Figure 1:
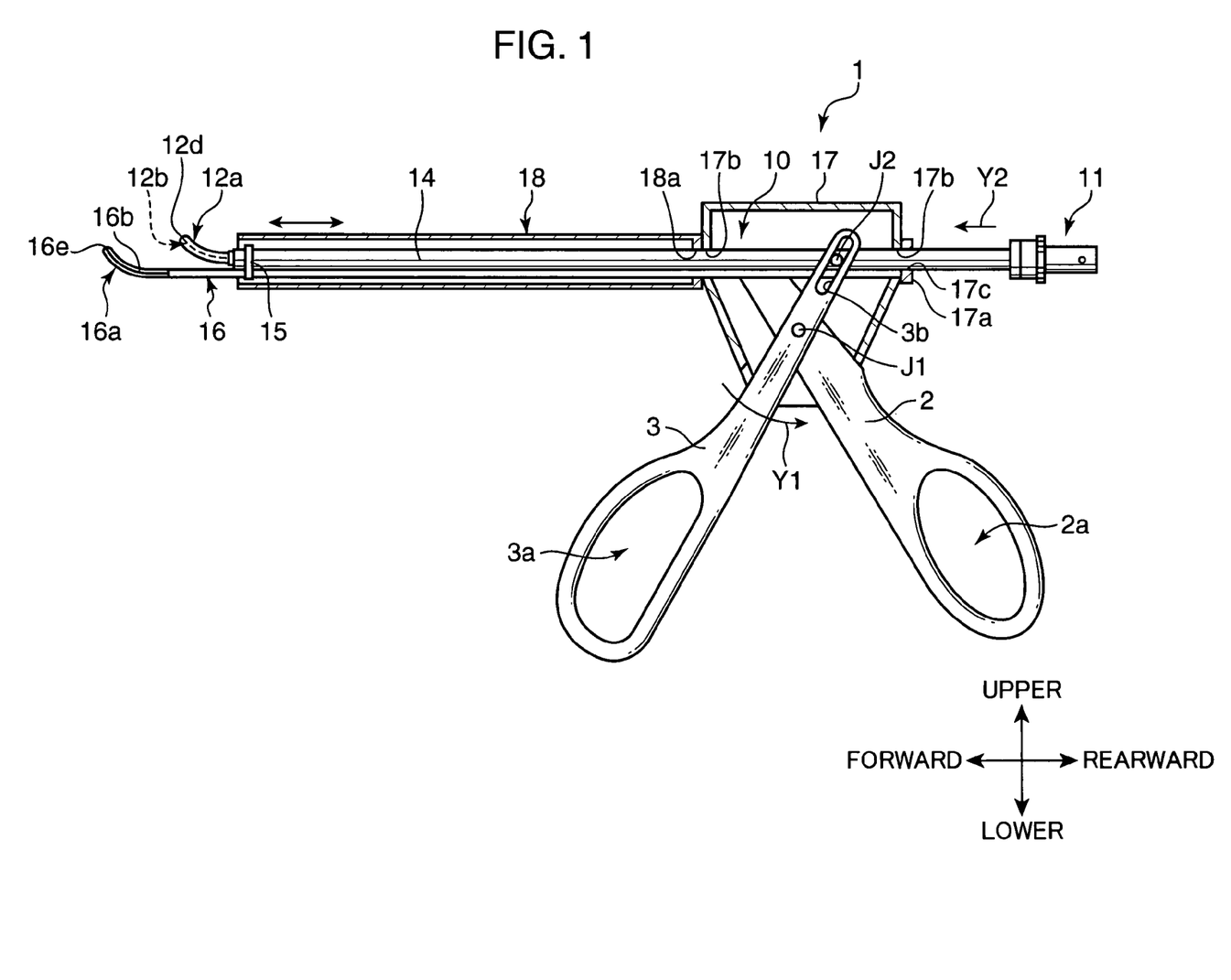
FIG. 1 is a partially sectional side view showing an entire structure of a medial treatment instrument according to an embodiment of the present invention.

FIG. 1 is a partially sectional side view showing an entire structure of a medical treatment instrument according to an embodiment of the present invention.

Referring to FIG. 1, a medical treatment instrument 1 includes a stationary handle 2, and a pivotal handle 3 attached to the stationary handle 2 pivotally about a pin J1. It should be noted that in the following description, the side at which the pivotal handle 3 is located with respect to the medical treatment instrument 1 is tentatively referred to as a forward side, and the side at which grip portions 2a and 3a of the stationary handle 2 and the pivotal handle 3 are located with respect to the medical treatment instrument 1 are tentatively referred to as a downward side.

The upper end portion of the pivotal handle 3 is formed with an elongated hole 3b extending longitudinally. A pin J2 is penetratedly inserted into the elongated hole 3b in parallel with the pin J1 in such a way that the pin J2 fixedly attached to a coaxial electrode unit 10 is slidable and rotatable.

Figure 2:
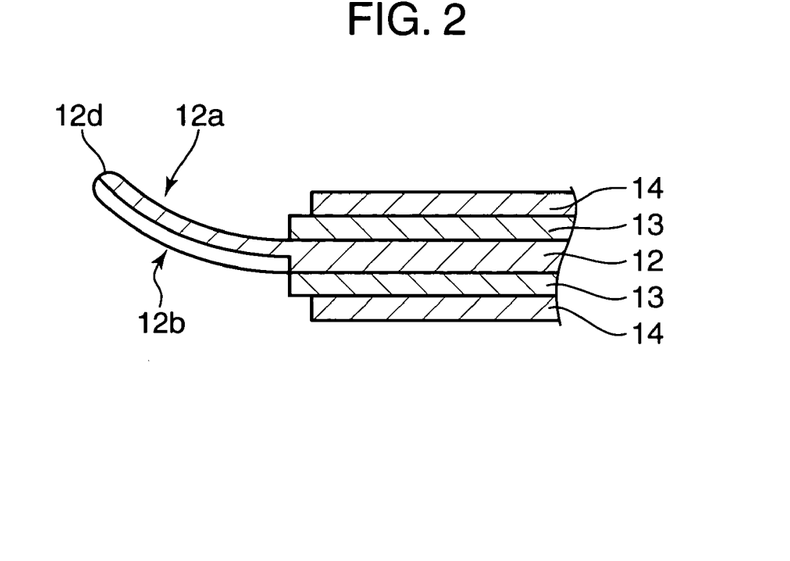
FIG. 2 is a sectional side view showing a frontal end portion of a coaxial electrode unit shown in FIG. 1.

The coaxial electrode unit 10 is a substantially cylindrical member extending in a forward and backward direction. As shown in FIGS. 1 and 2, the coaxial electrode unit 10 includes a connector 11 located at a rear end of the coaxial electrode unit 10 and connectable with an unillustrated high-frequency power source, a central conductor 12 (a first conductor) to be connected to the high-frequency power source, an insulator 13 (an insulating layer) covering the outside of the central conductor 12, and an outer conductor 14 covering the outside of the insulator 13 and located coaxially with the central conductor 12. In the coaxial electrode unit 10, when the connector 11 is connected with the high-frequency power source, a high-frequency voltage is applied to the central conductor 12 and the outer conductor 14. At this time, the outer conductor 14 is electrically connected with the ground side of the high-frequency power source.

Figure 3:
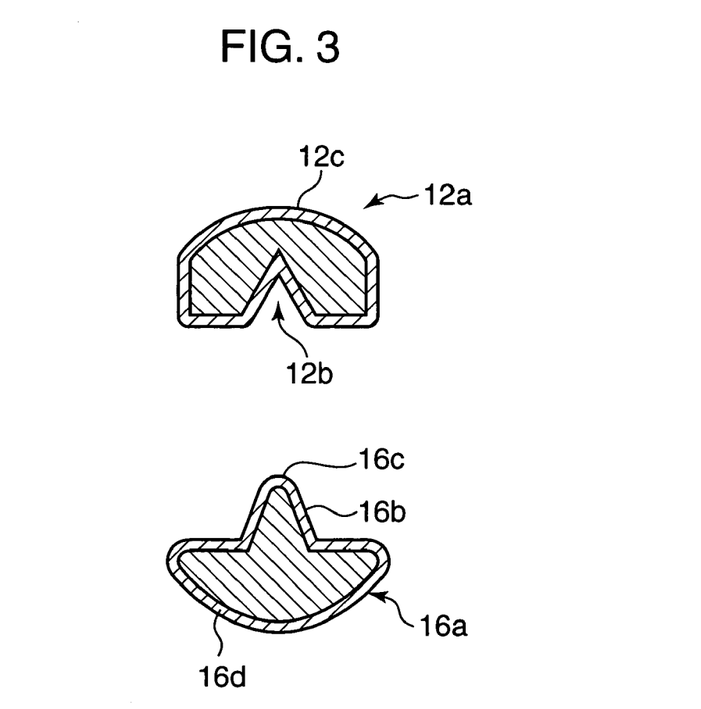

The central conductor 12 is made of copper plated with gold or silver, or a copper alloy such as phosphor bronze. The central conductor 12 is arranged in a state that its front end portion projects forward beyond the insulator 13 and the outer conductor 14 and curving upward with respect to the axial direction of the central conductor 12. The curved portion constitutes a central electrode 12a. The central electrode 12a curves with respect to the axis of the central conductor 12 at an angle properly set in accordance with the size of a biotissue to be treated, and preferably curves at an inclination of 10° to 50°, and in the illustrated example, curves at an inclination angle of substantially 30°. Further, as shown in FIGS. 2 and 3, the central electrode 12a is formed with a recess 12b having an inverted-V shape and extending along the lower curved surface of the central electrode 12a. The central electrode 12a is coated with a cover film 12c made of fluorine resin (PTFE) for coating the central electrode 12a. Further, a top end portion of the central electrode 12a is formed with a round portion 12d. This round portion 12d serves to reduce the damage to the biotissue when the central electrode 12 comes into contact with the biotissue.

The insulator 13 is made of fluorine resin (PTFE), and is formed into a pipe capable of covering the central conductor 12.

The outer conductor 14 is made of gold-plated yellow copper, and its front end portion is located at a position slightly rearward than the insulator 13. In the vicinity of the front end portion of the outer conductor 14, a ring-shaped connecting member 15 made of conductive metal is arranged. The connecting member 15 is configured so as to tie the outer conductor 14 and a movable conductor (a second conductor) 16 into a bundle. The connecting member 15 is fixed to the outer conductor 14 and electrically connected thereto. Further, the connecting member 15 holds the movable conductor 16 below the outer conductor 14 in such a manner that the movable conductor 16 is movable in the forward and backward direction.

The movable conductor 16 is made of conductive metal, and is preferably made of a material identical to the material of the outer conductor 14, and is a rod-shaped member extending in the forward and backward direction. A front end portion of the movable conductor 16 is curved at a curvature radius larger than the central electrode 12a, and this curved portion constitutes an outer electrode 16a. The aforementioned curvature radius is set in correspondence with the curvature radius of the central electrode 12a in such a manner that the lower curved surface of the central electrode 12a are in contact with the upper curved surface of the outer electrode 16a when they are brought into contact with each other. The outer electrode 16a curves at an inclination angle of substantially 30° with respect to the axis of the movable conductor 16 in the same direction of the central electrode 12a (a proper inclination angle is set within the range identical to the central electrode 12a). As shown in FIGS. 1 and 3, the outer electrode 16a is formed with a projection portion 16b having an inverted-V shape and extending along the upper curved surface of the outer electrode 16a in such a manner that the projection portion 16b faces the recess portion 12b in the forward and backward direction. The upper end portion of the projection portion 16b, i.e., the forward end portion, is formed with a round portion 16c to thereby prevent the problem that the biotissue is damaged before coagulating, and consequently bleeds. Further, the outer electrode 16a is coated with a cover film 16d made of fluorine resin (PTFE) as is the case of the central electrode 12a. As shown in FIGS. 1 and 4, the top end portion of the outer electrode 16a is formed with a round portion 16e to thereby reduce the damage to the biotissue when the central electrode 16a comes into contact with the biotissue. In particular, when a separation treatment described later (see FIG. 6) is performed, the round portion 16e enables the central electrode 16a to be smoothly inserted into a hard biotissue. An intermediate portion of the movable conductor 16 is held on the upper end portion of the stationary handle 2. The rear end portion of the movable conductor 16 is in contact with the front surface of a positioning member 17a attached to a casing 17 which is provided so as to cover the respective upper end portions of the stationary handle 2 and the pivotal handle 3. In this manner, the rearward movement of the rear end portion of the movable conductor 16 is restricted.

The casing 17 is a hollow vessel formed into the shape of a trapezoid whose size reduces toward its bottom in the side view. The casing 17 is formed with a pair of front and rear through holes 17b through which the outer conductor 14 is placed slidably in the forward and backward directions and the movable conductor 16 is placed. A positioning member 17a is arranged outside the rear through hole 17b. The positioning member 17a is formed with a supporting hole 17c for supporting the outer conductor 14 slidably in the forward and backward direction. On the other hand, an enclosure 18 is attached to the outside of the forward through hole 17b to enclose the respective intermediate portions of the outer conductor 14 and the movable conductor 16.

The enclosure 18 is a closed-end cylindrical member, and its bottom is fixedly attached to the front surface of the casing 17, and is formed with a penetrating hole 18a through which the outer conductor 14 is placed from outside slidably in the forward and backward direction, and through which the movable conductor 16 is placed from outside. The outer conductor 14 and the movable conductor 16 are placed through the penetrating hole 18a with their peripheral surfaces kept airtight. Accordingly, for example, when the central electrode 12a and the outer electrode 16a are inserted into a patient's abdominal cavity, the enclosure 18 is inserted into a cylindrical trocar which is penetrated into the abdominal cavity. At this time, a sealing member provided to the trocar keeps the air-tightness between the outer peripheral surface of the enclosure 18 and the inner peripheral surface of the trocar, and the air-tightness inside the enclosure 18 is maintained, thereby making it possible to suppress influence of variations in the pressure in the abdominal cavity.

In the medical treatment instrument 1 configured as described above, as shown in FIG. 1, the coaxial electrode unit 10 relatively shifts forward with respect to the movable conductor 16 as shown in the arrow Y2 as the pin J2 shifts forward by turning the pivotal handle 3 about the pin J1 in the direction of arrow Y1. Consequently, the central electrode 12a comes close to the outer electrode 16a from the backside thereof. On the other hand, the coaxial electrode unit 10 shifts in the direction reverse to the arrow Y2, that is, the backward direction by turning the pivotal handle 3 in the direction reverse to the arrow Y1. Consequently, the central electrode 12a is moved away from the outer electrode 16a backward.

Next, a manner of using the medial treatment instrument 1 will be described with reference to FIG. 4.

Figure 4A:
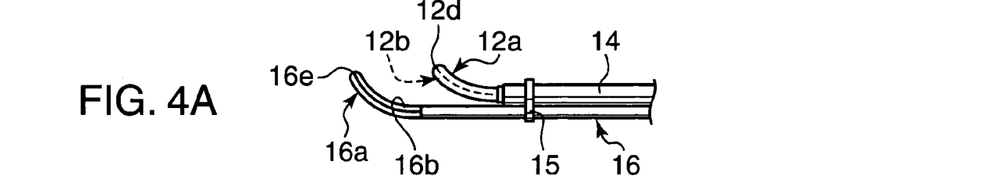
FIG. 4A shows a state before use.
Figure 4B:
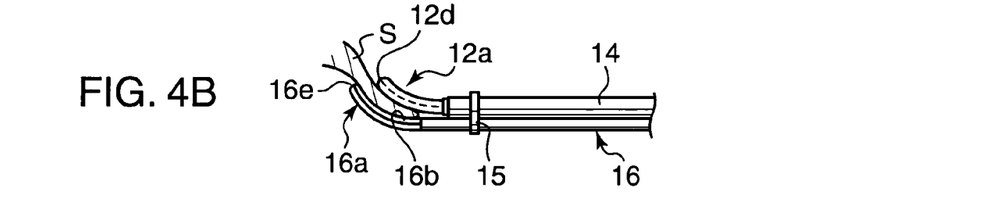
FIG. 4B shows a state where a biotissue is held.
Figure 4C:
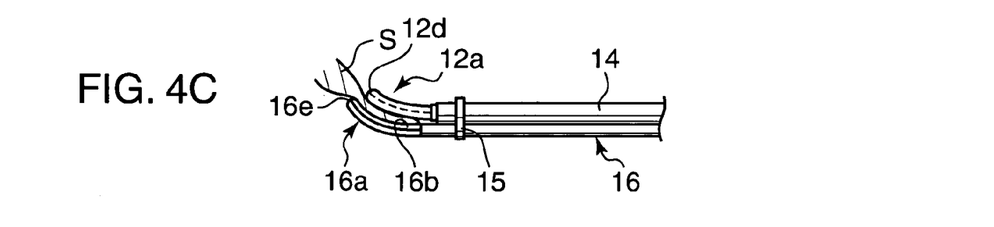
FIG. 4C shows a state where the biotissue is in coagulation.

First of all, as shown in FIG. 4A, the central electrode 12a and the outer electrode 16a which are apart from each other are guided to a biotissue S to be treated. The pivotal handle 3 is turned, and as shown in FIG. 4B, the biotissue S is held between the central electrode 12a and the outer electrode 16a. When the held biotissue S is coagulated, the pivotal handle 3 is further turned, and as shown in FIG. 4C, a microwave voltage is applied to the central electrode 12a and the outer electrode 16a while compressing the biotissue S therebetween. The vicinity electromagnetic field generated by the microwave electric power between the central electrode 12a and the outer electrode 16a generates dielectric heat in the biotissue S, and thus-generated dielectric heat coagulates the biotissue S.

Figure 4D:
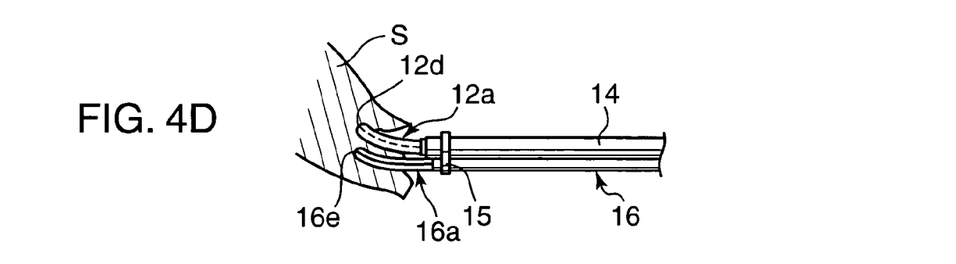
FIG. 4D shows a state where the cutting of the biotissue is started.
Figure 4E:
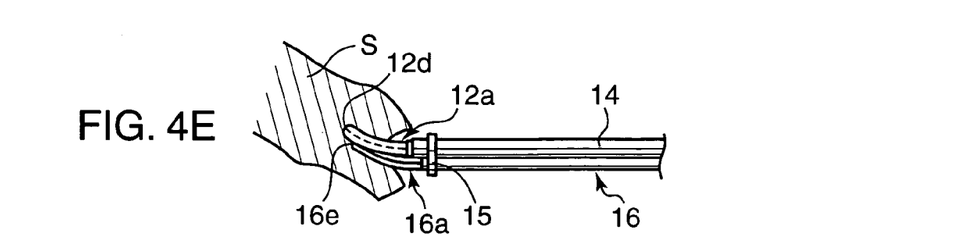
FIG. 4E shows a state where the biotissue is cut, respectively.

Next, when the biotissue S is cut, the pivotal handle 3 is further turned from the coagulating treatment state shown in FIG. 4C so that the central conductor 12 and the movable conductor 16 relatively shift in the axial direction. Thus, as shown in FIG. 4D, the central electrode 12a and the outer electrode 16a relatively shifts along their inclination angles as they grip the biotissue S, and slide in the directions against the biotissue S. As a result, as shown in FIG. 4E, the biotissue S is cut.

Figure 5A:
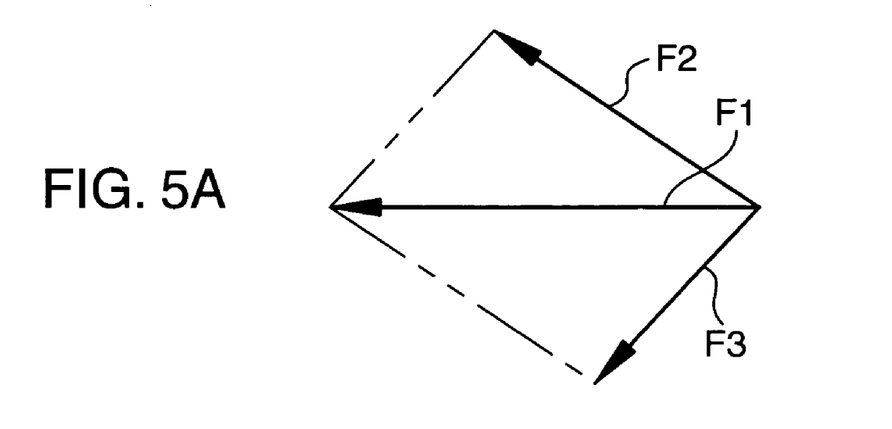
FIG. 5A shows a state where a force in the forward and backward direction is divided.
Figure 5B:
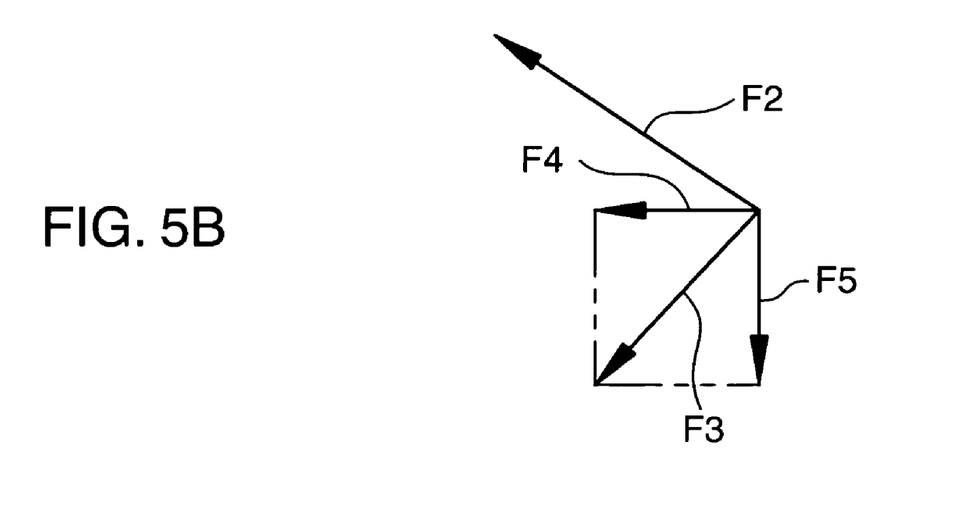
FIG. 5B shows a state where a force in the downward direction is divided.
Figure 5C:
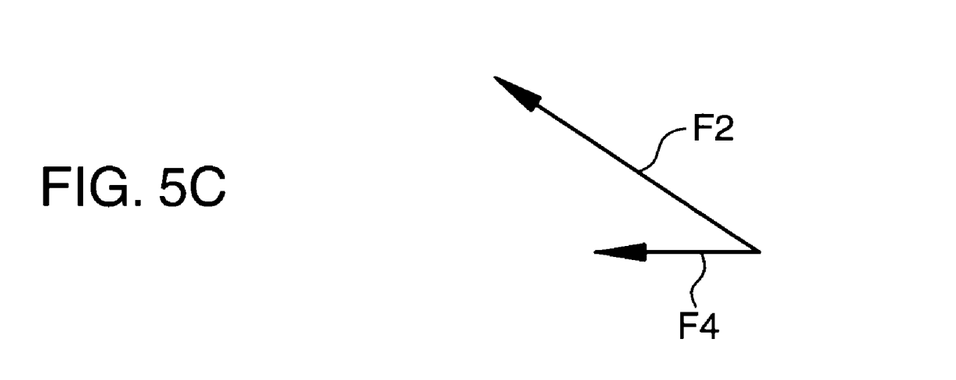
FIG. 5C shows a force applied to a biotissue when cutting is performed, respectively.

Specifically, when the cutting treatment as described above is performed, a force F1 generated in the forward direction by the turning of the pivotal handle 3 is divided into a force component F3 and a force component F2 applied along the curved surface of the outer electrode 16a. The force component F3 includes, as shown in FIG. 5B, a force component F4 in the forward direction and a force component F5 in a downward direction. Accordingly, as shown in FIG. 5C, the biotissue is subjected to the force component F4 in the forward direction generated between the central electrode 12a and the outer electrode 16a, that is, the force holding the biotissue S between the central electrode 12a and the outer electrode 16a, and the force component F2 along the curved surface of the outer electrode 16a, that is, the frictional force generated between the central electrode 12a and the outer electrode 16a. The medical treatment instrument 1 cuts the biotissue S by the force component F2 while gripping the biotissue S by the force component F4.

Further, the medical treatment instrument 1 may alternatively be used in the way shown in FIG. 6. In FIG. 6, description will be made about a case that there is a relatively large treatment target site Si in the surface of the biotissue S.

Figure 6A:
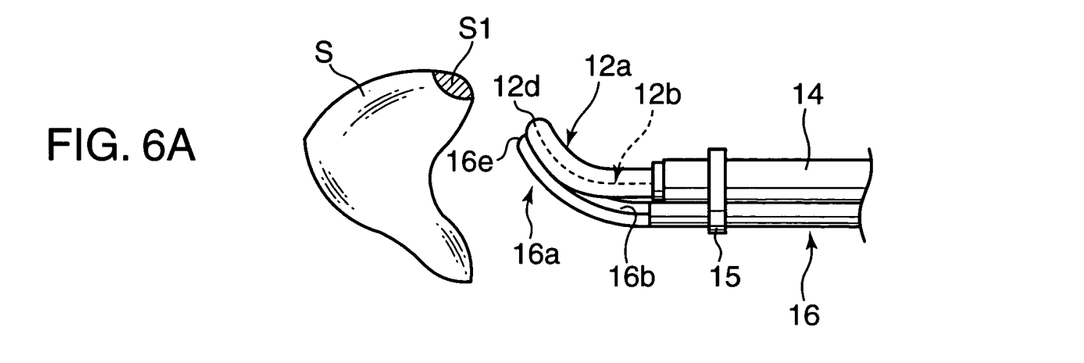
FIG. 6A shows a state before use.
Figure 6B:
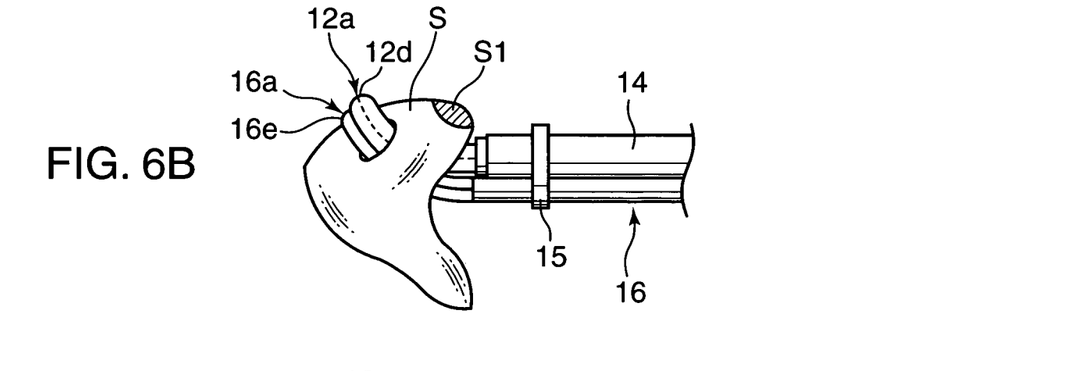
FIG. 6B shows a state where the medial treatment instrument is inserted into a biotissue.
Figure 6C:
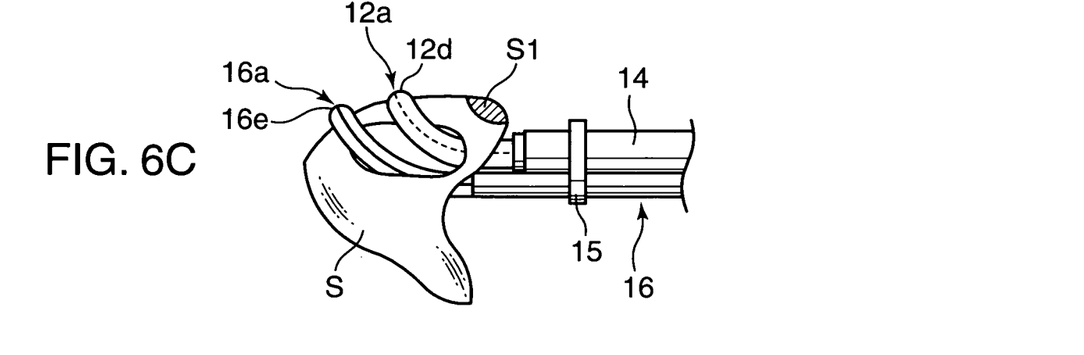
FIG. 6C shows a state where the electrodes are taken away from each other.
Figure 6D:
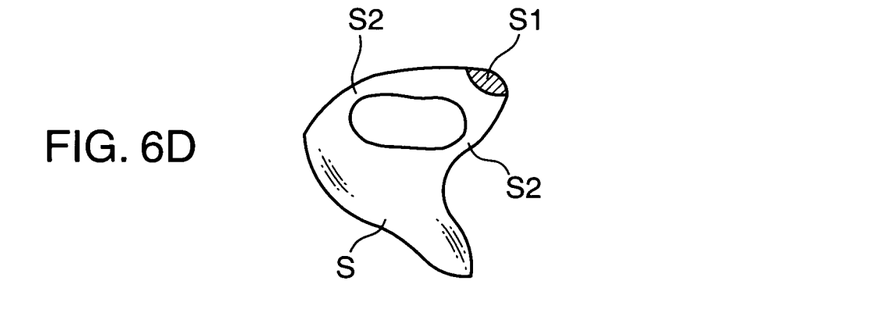
FIG. 6D shows a state of the biotissue separated from the medical treatment instrument, respectively.

First of all, as shown in FIG. 6A, the central electrode 12a and the outer electrode 16a in contact with each other are guided to the biotissue S to be treated. Then, the electrodes 12a, 16a are penetrated through the biotissue S in such a way that they come the backside of the treatment target site S1 (FIG. 6B). In this state, the pivotal handle 3 is operated to move away the central electrode 12a and the outer electrode 16a from each other as shown in FIG. 6C. As a result, the biotissue S is retained on the curved outer surfaces of the electrodes 12a, 16a inclined toward the separating direction (toward the forward and backward direction in FIG. 1). Thus, as the electrodes 12a, 16a are moved away from each other, the site located at the inner side of the curved surface of the electrodes 12a, 16a (the site including the treatment target site S1) can be separated from the biotissue S located at the outer side of the curved surface of the electrodes 12a, 16a (hereinafter, this state is referred to as separation). In many cases, thus-separated target site S1 remains connected with the biotissue S via a leg portion S2, as shown in FIG. 6D. In this case, the leg portion S2 is coagulated and cut by the manner shown in FIGS. 4. Consequently, the treatment target site S1 can be cut off from the biotissue S. Alternatively, by pinching the treatment target site S1 by the central electrode 12a and the outer electrode 16a in the state shown in FIG. 6D, the treatment target site S1 can be directly coagulated or cut.

As described above, according to the medical treatment instrument 1, the central conductor 12 and the movable conductor 16 are relatively shifted in the forward and backward direction (axial direction), so that the curved surfaces of the central electrode 12a and the outer electrodes 16a come close to each other to grip the biotissue S by the central electrode 12 and the outer electrode 16a. By applying a microwave voltage to the central electrode 12a and the outer electrode 16a in this state, the biotissue S can be coagulated. After the coagulation, the central conductor 12 and the movable conductor 16 are relatively shifted in the same forward and backward direction. Thus, the central electrode 12a and the outer electrode 16a are relatively shifted in their curvature direction to cut the biotissue S held therebetween by rubbing the biotissue S between the opposed surfaces of the central electrode 12a and the outer electrode 16a.

Specifically, in the medical treatment instrument 1, by relatively shifting the central conductor 12 and the movable conductor 16 in the forward and backward direction, the biotissue S can be held and coagulated. Then, by further relatively shifting the central conductor 12 and the movable conductor 16 in the forward and backward direction, a part of the force F1 in the forward and backward direction is converted into the force F2 along the curved surfaces of the central electrode 12a and the outer electrode 16a, that is, into the force other than the force in the direction of gripping the biotissue S, and the central electrode 12a and the outer electrode 16a are relatively shifted in accordance with the force F2. Then, frictional force is applied to the biotissue S between the central electrode 12a and the outer electrode 16a so as to cut the biotissue S.

Therefore, the medical treatment instrument 1 is capable of gripping the biotissue S by a simple operation where the central conductor 12 and the movable conductor 16 are relatively shifted in the forward and backward direction, coagulating the biotissue S by applying a microwave voltage, and cutting the biotissue S by use of the microwave voltage (for coagulation) and the frictional force.

Depending on the thickness of the biotissue S, after the biotissue S is coagulated, the application of the microwave voltage for coagulation is stopped. Then, in this state, the central electrode 12a and the outer electrode 16a are relatively shifted along their curvature directions, thereby cutting the biotissue S by use of only the frictional force. Even in this case, by relatively shifting the central electrode 12a and the outer electrode 16a while applying a microwave voltage for coagulation as described above, the biotissue S can be cut more rapidly.

In the medical treatment instrument 1, the central electrode 12a and the outer electrode 16a are curved upward with respect to the axial directions of the central conductor 12 and the movable conductor 16. Owing to this construction, in a case where the treatment target site S1 is located at a deep portion of the biotissue S which is overlapped complicatedly, the electrodes 12a, 16a can be smoothly inserted (penetrated) into the biotissue S. At this time, damages and the like to the biotissue S interposed between the electrodes 12a, 16a can be suppressed and harmless and smooth penetration can be achieved. Then, the treatment target site S is held by the electrodes 12a, 16a which has reached the treatment target site S1 to be pulled toward the user. Alternatively, a microwave voltage is applied to the electrodes 12a, 16a to coagulate and cut the treatment target site S1.

Further, in the foregoing construction, since the central electrode 12a and the outer electrode 16a coming close to each other are generally curved, the electrodes 12a, 16a can be smoothly penetrated into the biotissue S. From thus-penetrated state, the electrodes 12a, 16a are moved away from each other, thereby establishing a separated state where a part of the biotissue S is separated from the remaining portions. Specifically, the central conductor 12 and the movable conductor 16 are relatively shifted in their axial directions in such a manner that the electrodes 12a, 16a move away from each other with the electrodes 12a, 16a inserted into the biotissue S. As a result, the biotissue S is retained on the outer curved surfaces of the electrodes 12a, 16a inclining with respect to the shifting directions, and the biotissue S located near the electrodes 12a, 16a and the biotissue located S apart from the electrodes 12a, 16a can be separated from each other to establish a separated state as the electrodes 12a, 16a are relatively shifted. Therefore, in the case where it is difficult to compressedly pinch the treatment target site S1 by the central electrode 12a and the outer electrode 16a, the treatment target site S1 can be separated from the biotissue S, and then the leg portion S2 that connects the treatment target site S1 with the biotissue S is coagulated and cut by the electrodes 12a, 16a, thereby cutting off the treatment target site S1 from the biotissue S. It is also possible to directly coagulate or cut the separated treatment target site S1 between the central electrode 12a and the outer electrode 16a.

In the medical treatment instrument 1, the curvature radii of the curved surfaces of the electrodes 12a, 16a facing each other are respectively set in such a manner that the curved surfaces of the electrodes 12a, 16a come in contact with each other along their respective curved surfaces when the central conductor 12 and the movable conductor 16 are relatively shifted in the axial directions. In this construction, since the central electrode 12a and the outer electrode 16a in contact with each other can be made into a compact form, these electrodes 12a, 16a can be inserted into the biotissue S more smoothly. Consequently, the biotissue S can be separated more easily.

The central electrode 12a and the outer electrode 16a are not limited to the curved shapes assuming a circular arc having a constant curvature radius, and alternatively, may be configured into a shape constituted by plural arcs having various curvature radii. The shapes of the central electrode 12a and the outer electrode 16a are properly selected to enable them to be inserted into the biotissue S.

In the medical treatment instrument 1, the central electrode 12a is formed with the recess portion 12b extending along the curved surface at its front end side, whereas the outer electrode 16a is formed with the projection portion 16b extending along the curved surface at its rear end side. The recess portion 12b and the projection portion 16b are arranged so as to face each other in the forward and backward directions, and at the same time, the recess portion 12b and the projection portion 16b are configured so as to grip the biotissue S therebetween. Owing to this construction, since the biotissue S can be pinched by the recess portion 12b and the projection portion 16b, movement of the biotissue S in the width directions of the central electrode 12a, and the outer electrode 16a can be restricted and the biotissue S can be reliably held, and in addition, the large contact areas of the central electrode 12a and the outer electrode 16a with the biotissue S can be ensured. Consequently, the area to be coagulated in the biotissue S can be enlarged. Further, since the central electrode 12a and the outer conductor 16a slide against the biotissue S pinched between the recess portion 12b and the projection portion 16b, a larger frictional force is generated by the central electrode 12a and the outer electrode 16a, thereby cutting off the biotissue S reliably.

Since the projection portion 16b is formed with the round portion 16c at its top end portion, it is possible to prevent the biotissue S from being damaged to bleed before the biotissue S is coagulated.

The medical treatment instrument 1 may further include a conductive outer conductor 14 which is electrically connected with the ground side of the high-frequency power source, covers the outside of central conductor 12 via the insulating layer 13, and is provided so as to be coaxial with the central conductor 12. The movable conductor 16 is configured so as to be relatively shiftable in the forward and backward direction with respect to the outer conductor while being in contact with the outer peripheral portion of the outer conductor 14. In this arrangement, the central conductor 12 and the outer conductor 14 can be formed to be located on the same axial line. In addition, the electromagnetic noise released from the central conductor 12 can be shielded by the outer conductor 14, thereby reducing the noise level. Therefore, in the case where the medical treatment instrument 1 is entirely made of non-magnetic metal such as phosphor bronze and the like, for example, the medical treatment instrument 1 can be preferably used in an environment where magnetic field is generated from an MRI system.

In the medical treatment instrument 1, the connecting member 15 is fixedly arranged in the vicinity of the front end portion of the outer conductor 16. Owing to this arrangement, when the movable conductor 16 and central conductor 12 are relatively shifted in such a manner that the central electrode 12a and the outer electrode 16a are slidably relatively shifted (see FIG. 4E), the microwave current path for the movable conductor 16 can be reduced in the microwave current path from the connecting member 15 to the outer electrode 16a. Consequently, the pole at the ground side of the high-frequency power source can be connected to the movable conductor 16 at the position immediately before the outer electrode 16a while maintaining the alignment of the impedance of the microwave current as much as possible. Therefore, when the biotissue S is cut, the reduction in the thermal energy caused between the central electrode 12a and the outer electrode 16a can be suppressed as much as possible, thereby cutting off the biotissue S more reliably.

In the case where the medical treatment instrument 1a is configured in such a manner that the coaxial electrode unit 10 is provided below the movable conductor 16, and the coaxial electrode unit 10 and the movable conductor 16 are relatively shiftable in the forward and backward direction, and in correspondence with the relative movement, the outer electrode 16a comes close to the central electrode 12a from its rear side and is moved toward the rear side of the central electrode 12a, it is preferable that the connecting member 15 is fixedly attached to the outer peripheral surface of the movable conductor 16, differing from the foregoing embodiment. When thus-configured medical treatment instrument 1a is used, as the outer conductor 14 and the movable conductor 16 are relatively shifted and the outer electrode 16a comes close to the central electrode 12a, the connecting member 15 also comes close to the central electrode 12a. In other words, as the conductors 14, 16 are relatively shifted, the connecting member 15 is relatively shifted with respect to the outer conductor 14. In thus-configured medical treatment instrument 1a, the connecting member 15 is located in the vicinity of the top end portion of the outer conductor 14 in a case where the outer conductor 14 and the movable conductor 16 are relatively shifted in such a manner that the central electrode 12a and the outer conductor 16a slide against the biotissue S. In this arrangement, at least when the biotissue S is cut, the reduction in the thermal energy generated between the central electrode 12a and the outer electrode 16a can be suppressed as much as possible, thereby cutting off the biotissue S more reliably.

Further, in both of the medical treatment instruments 1 and 1a, when the central electrode 12a and the outer electrode 16a are relatively shifted along the others' curved surfaces, the outer conductor 14 and the movable conductor 16 receive the force toward the direction along which the conductors 14, 16 are moved away from each other. The connecting member 15 serves to prevent the shift, and to allow the outer conductor 14 and the movable conductor 16 to come in contact with the connecting member 15 reliably owing to the force toward the direction along which the conductors 14, 16 moves away from each other. Thus, when the biotissue S is cut, the microwave voltage can be applied reliably between the central electrode 12a and the outer electrode 16a, thereby cutting of the biotissue S more reliably.

The medical treatment instruments 1 and 1a coagulate the biotissue S by utilizing the microwave voltage. The electrocalory induced from the nearby electromagnetic field generated by the microwave electric power can be applied to the biotissue S pinched by the central electrode 12a and the outer electrode 16a. Therefore, the biotissue S located within the nearby electromagnetic field can be coagulated without affecting the portion of the biotissue S located out of the nearby electromagnetic field.

Further, the biotissue S can be coagulated by evaporating the moisture from the biotissue S by the electrocalory induced from the nearby electromagnetic field generated by the microwave electric power. In this manner, the biotissue S can be mildly coagulated as compared with the case where the surface of the biotissue S is rapidly coagulated by Joule heat by use of a high-frequency voltage at a RF band having a main frequency of 500 KHz which is conventionally employed in a known electric surgical knife. Accordingly, the biotissue can be kept in a fixed state where its function is stopped while maintaining the cell shape of the biotissue S. Thus, it is possible to suppress the occurrence of problem where the rapid coagulation causes the coagulated surface to peel off and drop from the biotissue S. Further, after coagulated or fixed, the biotissue S is cut by the sliding movement created from the relative movement, and there is no need of additionally preparing a RF power source.

In the foregoing medical treatment instruments 1 and 1a, the stationary handle 2 is fixedly attached to the movable conductor 16. Alternatively, an elongated hole may be formed on the upper end portion of the stationary handle 2 as is the case of the pivotal handle 3; a shaft may be formed on an intermediate portion of the movable conductor 16; and by use of the elongated hole and the shaft, the movable conductor 16 may be supported by the shaft so as to be slidable with respect to the stationary handle 2. According to this construction, as the stationary handle 2 and the pivotal handle 3 are operated, the central electrode 12a and the outer electrode 16a can be brought close to each other while preventing the coaxial electrode unit 10 and the movable conductor 16 enclosed in the casing 17 from moving toward the direction perpendicular to their axial directions.

When the medical treatment instruments 1 or 1a is used in the case where a plurality of small holes are produced in the patient's body surface; abdominal cavity mirror made of a CCD camera and the like is inserted into one of the holes; and while observing the diseased area in the patient's body using the abdominal cavity mirror, a medical treatment instrument is inserted from the other hole to treat the diseased area, that is, in surgery under observation using an abdominal cavity mirror, the diseased area can be held, coagulated, and cut using one and the same apparatus. This eliminates the need of inserting and extracting treatment instruments in accordance with these operation steps. Consequently, the time required for the surgery can be significantly reduced and invasion to the patient can be reduced as much as possible.

Further, since the microwave has the characteristic of being easily regulatable in high frequencies, the medical treatment instruments 1 or 1a may be miniaturized so as to be used for application where it is passed through an opening of a forceps, and manipulated under observation using the endoscope, and further miniaturized so as to be used for application where it is inserted into a blood vessel.

Further, although the microwave voltage is applied to the medical treatment instrument 1 in the foregoing embodiment, the present invention is not limited thereto. Alternatively, for example, the biotissue S can be coagulated and cut by applying to the medical treatment instrument 1 a high-frequency voltage of a RF band having a main frequency of 500 KHz which has a lower frequency than the microwave and is employed in a known electric surgical knife and the like.

Further, in the foregoing embodiment, the central conductor 12 (coaxial electrode unit 10) is configured so as to be shiftable in the forward and backward direction with respect to the movable conductor 16. Alternatively, the movable conductor 16 may be configured so as to be shiftable in the forward and backward direction or both of the central conductor 12 and the movable conductor 16 may be shiftable.

Further, in the foregoing embodiment, although the central conductor 12 (first conductor) and the outer conductor 14 are coaxially formed and the movable conductor 16 (second conductor) is electrically connected to the outer conductor 14, the present invention is not limited thereto. Alternatively, for example, the first conductor and the second conductor may be configured so that they are formed on their respective axial line, and are connected to a high-frequency power source and arranged in parallel to each other in an insulated state, and thus-configured conductors are relatively shifted.

In the foregoing embodiment, although the pivotal handle 3 is turned in the forward and backward direction to relatively shift the central conductor 12 and the outer conductor 14, the present invention is not limited thereto. Alternatively, for example, an arrangement shown in FIG. 7 may be employed. The same components as those of the foregoing embodiment are denoted by identical reference numerals, and description of them is omitted. Further, in FIG. 7, in the following description, a direction perpendicularly intersecting the upward and downward direction and the forward and backward direction is a left and right direction.

Figure 7:
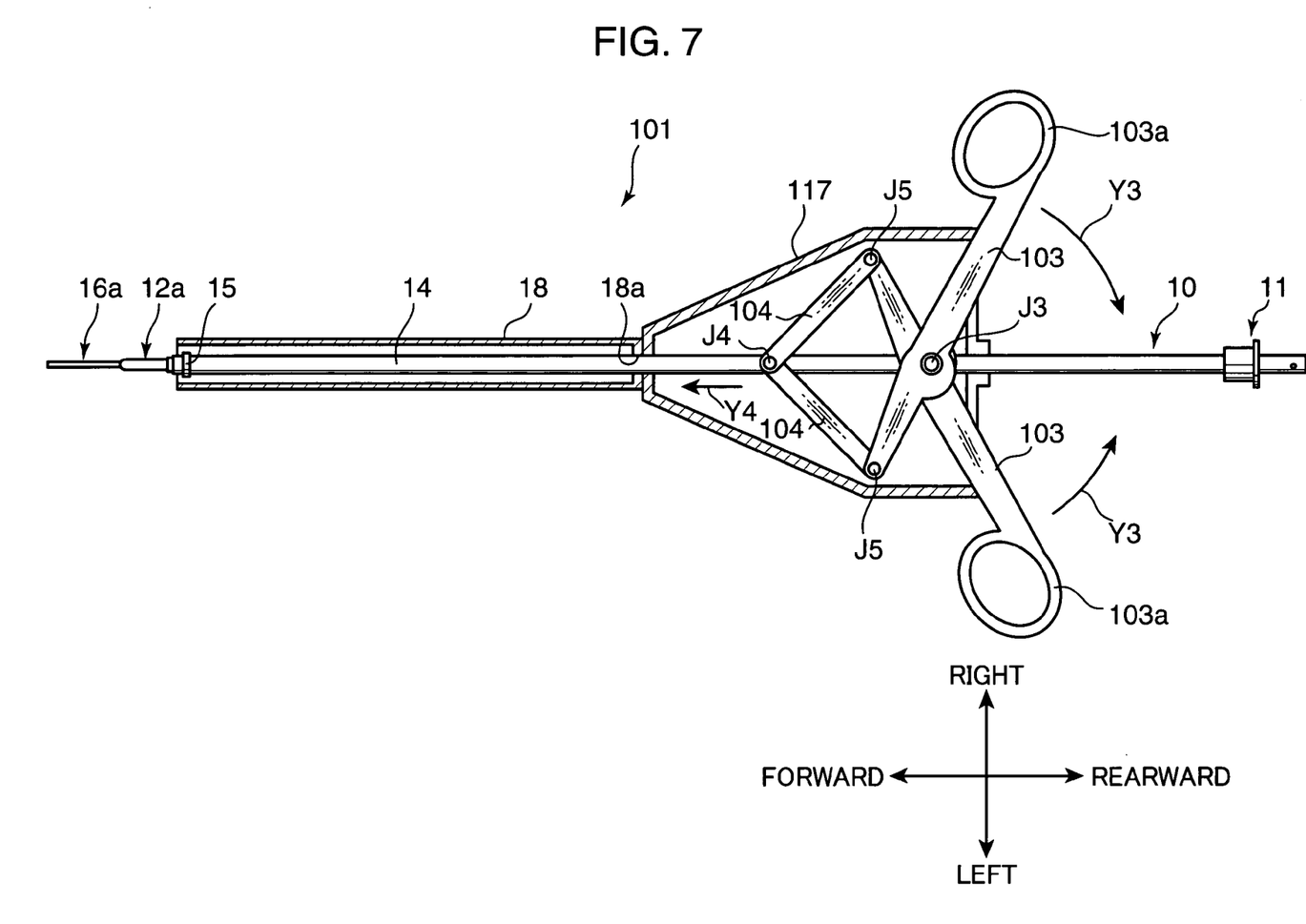
FIG. 7 is a partially sectional plan view showing an entire structure of a medical treatment instrument according to another embodiment.

A medical treatment instrument 101 includes a casing 117 fixedly attached to a back surface of an enclosure 18, a pin J3 provided in the casing 117, a pair of left and right pivotal handles 103 turnable about the shaft J3, a pair of levers 104 connecting the pivotal handles 103 and the outer conductor 14, and a pin J4 provided on an outer conductor 14 in front of the pivotal handles 103. The pin J3 extends in an upper and lower direction in the casing 117, and supports the pivotal handles 103 in such a manner that they cross with each other. Each of the pivotal handles 103 includes a gripping portion 103a formed at its rear end portion, and a pin J5 extending in an upper and lower direction at its front end portion. The front end portion of each lever 104 is pivotally attached to the pin J4 extending in an upper and lower direction, whereas the rear end portion of each lever 104 is attached to the pin J5 of the pivotal handle 103 in a state where the levers 104 are pivotable independently of each other.

In thus-configured medical treatment instrument 101, as shown in the arrow Y3, the pivotal handles 103 are turned in the direction in which the gripping portions 103a of the pivotal handles 103 come close to each other, so that the rear end portions of the lever 104 come close to each other. In response to this movement, the front end portions of the levers 104 are pushed forward as shown by the arrow Y4. Consequently, the outer conductor 14 is shifted forward to allow the central electrode 12a and the outer electrode 16a to come close to each other. On the other hand, the pivotal handles 103 are turned in the direction reversal to the arrow Y3, so that the central electrode 12a and the outer electrode 16a move away from each other. Consequently, the medical treatment instrument 101 can grip, coagulate, and cut the biotissue S in the method shown in FIG. 4, and also can separate the treatment target site S1 in the method shown in FIG. 6.

Figure 8:
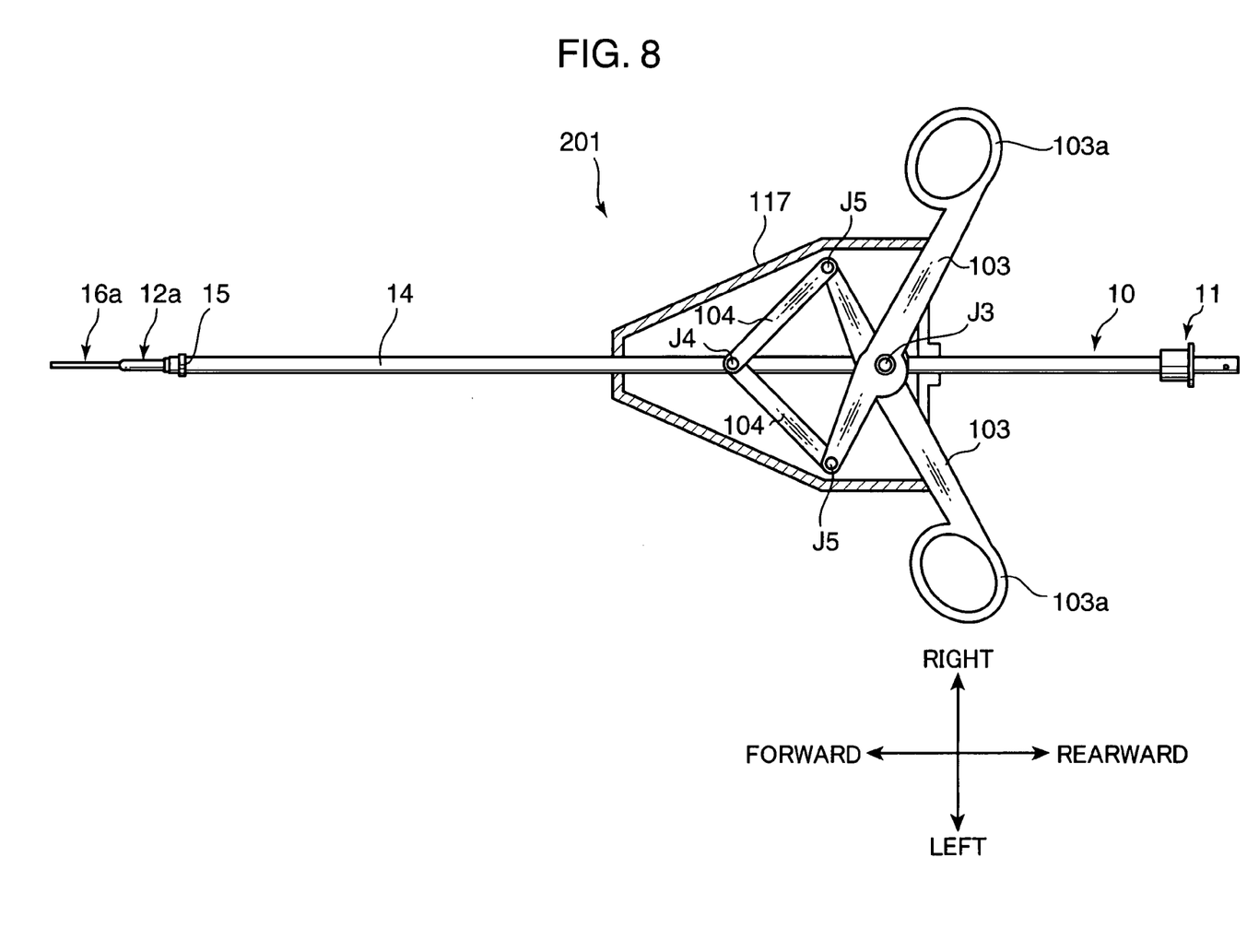
FIG. 8 is a view showing a modification of the instrument shown in FIG. 7.

By the way, the medical treatment instruments 1 and 101 have an enclosure for the purpose of being used in the manipulation within the patient's abdominal cavity. Alternatively, for example, when the medical treatment instruments 1 and 101 are used in the manipulation during an abdominal operation, the enclosure 18 may be omitted as shown in FIG. 8. According to the medical treatment instrument 201, the construction can be simplified, thereby reducing the cost.

Figure 9:
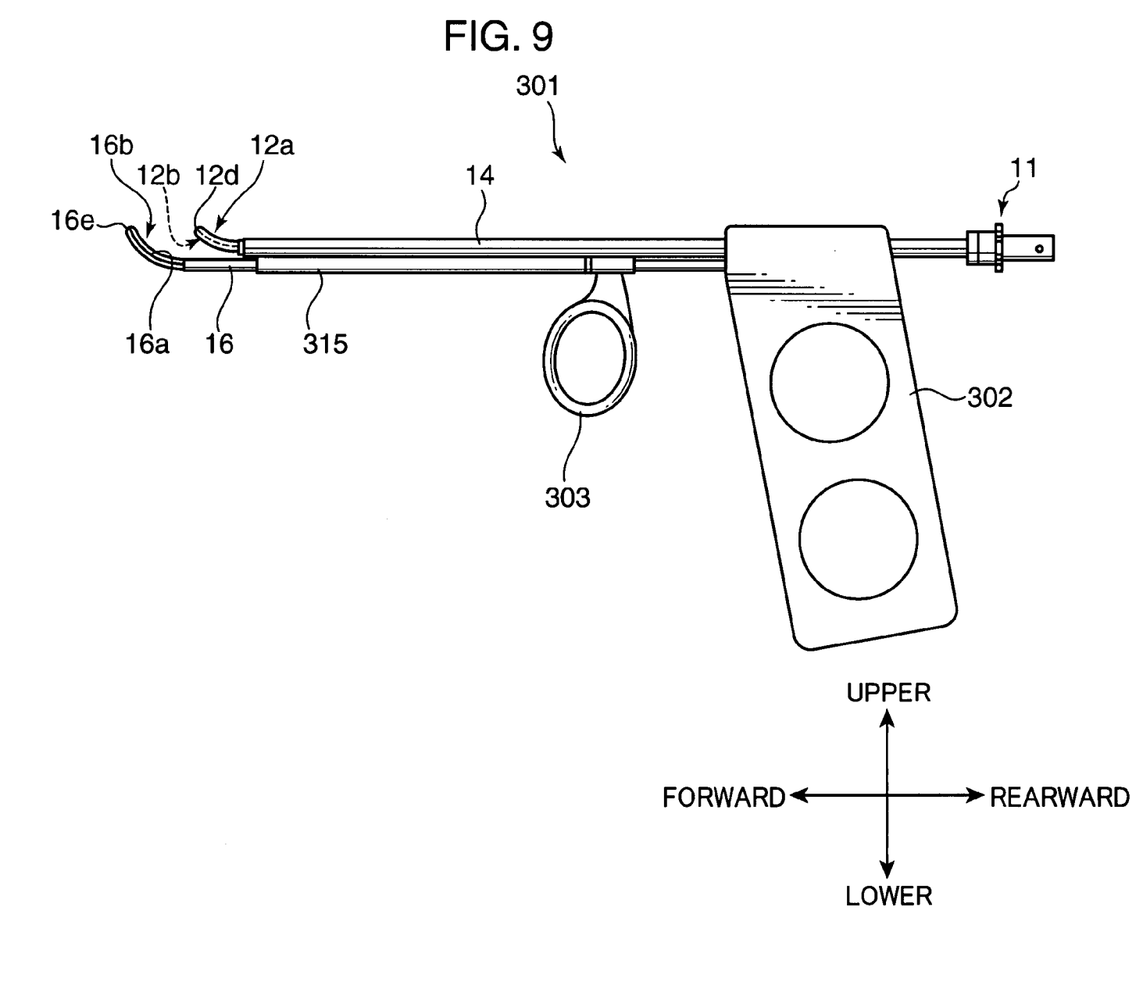
FIG. 9 is a side view showing an entire structure of a medial treatment instrument according to still another embodiment.

Further, as a medical treatment instrument to be used in a manipulation during an abdominal operation, it may be appreciated to use a configuration of a pistol shape, as shown in FIG. 9. FIG. 9 is a side view similar to FIG. 1.

A medical treatment instrument 301 includes a handle portion 302 fixedly attached to an outer conductor 14, a connecting member 315 longer than the connecting member 15 in the forward and backward direction, and a trigger portion 303 fixedly attached to the movable conductor 16. The trigger portion 303 is relatively shifted with respect to the handle portion 302 to thereby cause the central electrode 12a and the outer electrode 16a to come close to each other. According to the medical treatment instrument 301, the number of members can be further decreased, thereby reducing the cost as low as possible.

Figure 10:
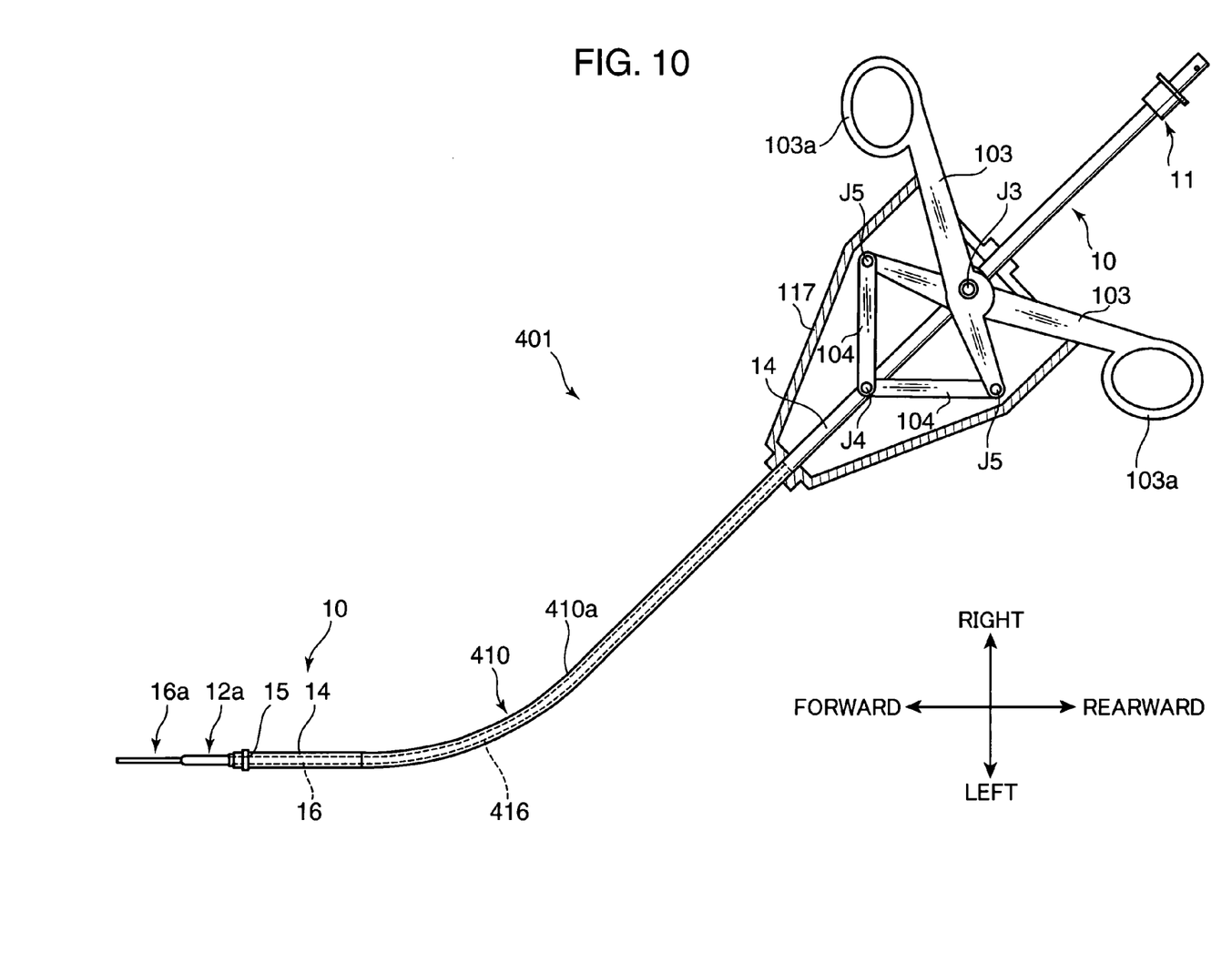
FIG. 10 is a partially sectional plan view showing an entire structure of a medical treatment instrument according to yet still another embodiment.

Further, in the medical treatment instruments 1, 101, 201, 301, the coaxial electrode unit 10 and the movable conductor 16 are made to have relatively rigidity. Alternatively, as shown in FIG. 10, the coaxial electrode unit 10 and the movable conductor 16 may be made to have flexible intermediate portions.

A medical treatment instrument 401 includes a flexible unit 410 and a flexible conducting portion 416 formed in intermediate portions of the coaxial electrode unit 10 and the movable conductor 16 of the medical treatment instrument 201 shown in FIG. 8. The flexible unit 410 has flexibility achieved by making the outer conductor 14 by a braided wire, instead of the laminated structure shown in FIG. 2, to set the diameter of the central conductor 12 relatively small, or making the central conductor 12 by a twisted wire made of a plurality of conductive wires each having a relatively small diameter. A covering layer 410a made of fluorine resin (PTFE) or a synthetic resin is formed on outside the braided wire. The flexible conducting portion 416 has the flexibility achieved by making the outer conductor 16 by a braided wire. In the medical treatment instrument 401, it may be preferable to make the flexible unit 410 and the flexible conducting portion 416 run along the axial direction, and provide a tube made of a fluorine resin (PTFE) and the like on the outside of the flexible unit 410, and make the flexible conducting portion 416 slide in the tube. Alternatively, the tube and the flexible unit 410 may be covered together with a covering member similar to the covering layer 410a. The length and outer diameter of the flexible unit 410 and the flexible conducting portion 416 may be properly set so as to be suitable for the surgical operations to which the medical treatment instrument 401 is employed. Still alternatively, the medical treatment instrument 401 may be used in a state where it is passed through a (rigid or flexible) endoscope.

According to the medical treatment instrument 401, the flexible unit 410 and the flexible conducting portion 416 flexibly deform in accordance with the portion where they are inserted. Therefore, for example, the treatment target site S1 located inside intestinal canals or blood vessels can be easily held, coagulated, cut, and then separated by inserting the central electrode 12a and the outer electrode 16a into complicatedly curved intestinal canals or blood vessels.

In the medical treatment instruments 1, 101, 201, 301, 401, the central electrode 12a and the outer electrode 16a are curved with respect to the axial direction of the central conductor 12 and the movable conductor 16. Therefore, for example, in the case that the treatment target site S1 is located inside a recess portion with a narrow entrance and a large inner space in the biotissue S, in other words, in the case that the treatment target site S1 is located in a diseased area having narrow entrance, during the operation in which both the conductors 12a, 16a are inserted into the diseased area to grip, fix, coagulate, and cut the treatment target site S1, by viewing the diseased area through the narrow entrance from above, a motion of the electrodes 12a, 16a curved with respect to the axial direction of the conductors 12, 16 can be easily observed over the wide range of the diseased area. In particular, the medical treatment instruments 101, 201, 401 (see FIGS. 7, 8, 10) are configured in such a manner that the pivotal handle 103 is turned in the direction (left and right direction) perpendicular to the curved direction (upper and lower direction) of the electrodes 12a, 16a to thereby cause the electrodes 12a, 16a to come close to each other. In this configuration, the treatment target site S1 can be treated without the problem that the pivotal handles 103 turned by the turning operation hides an entrance of a diseased area.

As described above, a tissue can be held by a simple operation of shifting the first conductor and the second conductor in the axial direction, and can be coagulated by applying a coagulation high-frequency voltage. Further, the biotissue can be cut by use of the high-frequency electric power for coagulation and a frictional force.

An inventive medical treatment instrument comprises a first conductor and a second conductor extending in parallel directions to each other and relatively shiftable in their axial directions, and a high-frequency voltage being applied to the top end portions of the conductors so as to coagulate and cut a biotissue held between a top end portion of the first conductor and a top end portion of the second conductor. The top end portion of the first conductor and the top end portion of the second conductor are inclined in the same direction with respect to the axial directions of the both conductors, and the relative shift of the conductors in their axial directions allows the top end portions of the both conductors to come close to each other to grip the biotissue therebetween, and the conductors are further relatively shifted in their axial directions to thereby shift the top end portions of the conductors relatively along the inclined directions with their top end portions gripping the biotissue, and slid against the biotissue in the same direction to cut the biotissue.

The first conductor and the second conductor are relatively shifted in the axial directions, so that the inclined surfaces of the conductors come close to each other to grip a biotissue between the top end portions of the both electrodes. By applying a coagulation high-frequency voltage to the conductors in this state, the biotissue can be coagulated. After the coagulation, the first conductor and the second conductor are further relatively shifted in the same axial directions to allow the top end portions of the conductors to relatively shift in the inclined directions, and thereby cutting the biotissue held therebetween by rubbing the biotissue against the opposed surfaces of the top end portions.

Specifically, in the medical treatment instrument, by relatively shifting the first conductor and the second conductor in the axial directions, the biotissue can be held and coagulated. Further relative shift of the conductors in the axial directions converts a part of the force applied in the axial direction into a force along the inclined surfaces of the top end portions of the conductors, that is, a force other than the force in the direction of gripping the biotissue. This force causes the top end portions of the conductors to relatively shift to each other, consequently generating a frictional force against the biotissue between the top end portions to cut the biotissue.

Accordingly, the medical treatment instrument makes it possible to grip the biotissue by the simple operation that the first conductor and the second conductor are relatively shifted in the axial directions, and to coagulate the biotissue by the coagulation high-frequency voltage, and to cut the biotissue by use of the coagulation high-frequency voltage and the frictional force.

The high-frequency voltage used here means a range of high-frequency voltages from a whole microwave band having a main frequency of 2.45 GHz to a RF band having a main frequency of 500 KHz.

In the medical treatment instrument, it may be preferable that the top end portion of the first conductor and the top end portion of the second conductors are curved in the same direction with respect to the axial direction of the conductors.

According to the configuration in which the top end portions of the first conductor and the second conductor are curved, for example, even in the case where the treatment target site is located at a deep portion of the biotissue which is overlapped complicatedly, the top end portions of the first and second conductors can be smoothly inserted (hereinafter, referred to as penetration. The word "penetration" means not only insertion of the first or second conductors into a gap between independent biotissues, but also insertion of the first or second conductors into a single biotissue). At this time, damages and the like to biotissues located on sides of the conductors can be suppressed, and harmless and smooth penetration can be achieved. The treatment target site can be held by the top end portions of the first and second conductors which have reached the treatment target site, and be pulled toward the user. Alternatively, a high-frequency voltage is applied to the conductors to coagulate and cut the treatment target site.

Further, in the above construction, the first and second conductors are penetrated into the biotissue to separate a part of the biotissue. Specifically, since the top end portions of the first and second conductors coming close to each other have a curved shape as a whole, the top end portions of the conductors can be smoothly penetrated into the biotissue. From thus-penetrated state, the top end portions of the conductors are moved away from each other, thereby establishing a separated state where a part of the biotissue is separated from the remaining portions. Specifically, the conductors are relatively shifted in their axial directions in such a manner that the top end portions of the conductors move away from each other with the first and second conductors being inserted into the biotissue. Consequently, the biotissue is retained on the outer curved surfaces of the conductors inclining with respect to the shifting directions, and the biotissue located near the conductors and the biotissue located apart from the conductors can be separated from each other to establish a separated state as the conductors are relatively shifted. Therefore, in the case where it is difficult to pinch the treatment target site by the top end portions of the first and second conductors (for example, in the case where the treatment target site is relatively large in size), the treatment target site can be separated from the biotissue, and then the linking portion that links the treatment target site with the biotissue is pinched by the top end portions of the first and second conductors, coagulated and cut, thereby separating the treatment target site from the biotissue. It is also possible to directly coagulate or cut the separated treatment target site between the first and second conductors.

In the medical treatment instrument, it may be preferable that the curvature radii of the top end portion of the first conductor and the top end portion of the second conductor are set in such a manner that, when the conductors are relatively shifted in the axial directions, the curved surfaces of the top end portions of the conductors facing each other come in contact with each other along each others' curved surfaces.

In the configuration in which the top end portions of the first and second conductors come in contact with each other along the others' curved surfaces, since the top end portions of the first and second conductors in contact with each other can be made into a compact form, these conductors can be inserted into the biotissue more smoothly. Accordingly, the biotissue can be separated more easily without invasion to the biotissue.

In the medical treatment instrument, it may be preferable that a surface of the top end portion of either one of the first conductor and the second conductor facing each other is formed with a recess portion extending along the inclined surface of its conductor, whereas the remaining surface is formed with a projection portion extending along the inclined surface of its conductor, and the recess portion and the projection portion are arranged so as to face each other in the axial directions of the conductors, and the recess portion and the projection portion are configured so as to grip a biotissue therebetween.

In the configuration including the recess portion and the projection portion, since the biotissue can be pinched between the recess portion and the projection portion, the movement of the biotissue in the width directions of the conductors can be restricted and the biotissue can be reliably held, and in addition, the large contact areas of the top end portions of the conductors with the biotissue can be ensured. Accordingly, the area to be coagulated in the biotissue can be increased. Further, since the top end portions of the conductors slide against the biotissue pinched by the recess portion and the projection portion, a larger frictional force is generated by the top end portions of the conductors, thereby cutting off the biotissue reliably.

Since the biotissue is compressedly pinched by the recess portion and the projection portion to be coagulated, it may be preferable that the projection portion is formed with a round portion at its top end portion. In this arrangement, it is possible to prevent the biotissue from being damaged to bleed before the biotissue is coagulated.

The medical treatment instrument may be further provided with a conductive outer conductor electrically connected to a ground of a high-frequency power source, coating the outside of the first conductor via an insulating layer, and arranged coaxially with the first conductor. The second conductor is configured so as to be relatively shiftable in its axial direction with respect to the outer conductor while being in contact with the outer peripheral portion of the outer conductor.

In the configuration where the outer conductor and the second conductor are relatively shiftable, the first conductor and the outer conductor can be formed on the same axial line. In this arrangement, electromagnetic noises radiated from the first conductor can be shielded by the outer conductor, thereby reducing the noise level. Therefore, in the case that the medical treatment instrument is entirely made of non-magnetic metal such as phosphor bronze and the like, for example, the medical treatment instrument can be preferably used in an environment under the magnetic field of an MRI system.

The medical treatment instrument may be further provided with a conductive connecting member for connecting the outer conductor with the second conductor in a relatively shiftable manner. The connecting member is configured so as to be arranged in the vicinity of the top end portion of the outer conductor when the outer conductor and the second conductor are relatively shifted in such a manner that at least the top end portions of the first conductor and the second conductor slid against the biotissue.

Owing to the configuration including the connecting member, in the high-frequency current path from the connecting member to the top end portion of the second conductor, the path to the second conductor can be reduced. Accordingly, the ground of the high-frequency power source can be connected to the second conductor at the position immediately before the top end portion of the second conductor while maintaining the alignment of the impedance of the high-frequency power source as much as possible. Therefore, when the biotissue is cut, the reduction in the thermal energy caused between the top end portions of the conductors can be suppressed as much as possible, thereby cutting off the biotissue more reliably.

Alternatively, an inventive medical treatment apparatus comprises the above-mentioned medical treatment instrument connected with a high-frequency power source capable of supplying microwave electric power. The high-frequency power source applies a microwave voltage to the top end portion of the first conductor and the top end portion of the second conductor, so that the biotissue held by the top end portions of the conductors is fixed, coagulated, and then cut.

According to the medical treatment apparatus, the dielectric heat induced from the nearby electromagnetic field generated by the microwave electric power can be applied to the biotissue pinched by the top end portions of the conductors. Accordingly, the biotissue located within the nearby electromagnetic field can be coagulated without affecting the portion of the biotissue located out of the nearby electromagnetic field.

Further, in the medical treatment apparatus, the biotissue can be coagulated by evaporating moisture from the biotissue by the dielectric heat induced from the nearby electromagnetic field generated by the microwave electric power. In this manner, the biotissue can be mildly coagulated as compared with the case where the surface of the biotissue is rapidly coagulated by Joule heat by use of a high-frequency voltage at a RF band having a main frequency of 500 KHz which has been conventionally employed in the known electric surgical knife. Consequently, the biotissue can be kept in a fixed state where its function is stopped while maintaining the cell shape of the biotissue. Thus, it is possible to suppress the occurrence of problem where the rapid coagulation causes the coagulated surface to peel off and drop from the biotissue. Further, after coagulated or fixed, the biotissue is cut by the sliding owing to the relative movement. Thus, there is no need of additionally providing a RF power source.

The microwave means a whole microwave band having a main frequency of 2.45 GHz.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

The invention claimed is:

1. A medical treatment instrument comprising a first conductor and a second conductor extending in parallel directions to each other and relatively shiftable in their axial directions, each conductor comprising an electrode located at a top end portion of the conductor, and a high-frequency voltage being applied to each top end portion of the conductors so as to coagulate and cut a biotissue held between the top end portion of the first conductor and the top end portion of the second conductor, wherein the top end portion of the first conductor and the top end portion of the second conductor are inclined in the same direction with respect to the axial directions of the conductors, such that when the conductors are relatively shifted in their axial direction the top end portions of the conductors come close to each other to grip biotissue therebetween, and when the conductors are further relatively shifted in their axial direction the top end portions of the conductors slide against the biotissue and the electrodes generate a frictional force to cut the biotissue, wherein the top end portion of the first conductor and the top end portion of the second conductor are curved in the same direction with respect to the axial directions of the conductors, and having curvature radii of the top end portion of the first conductor and the top end portion of the second conductor that are different and are set in such a manner that, when the conductors are relatively shifted in the axial directions, the curved surfaces of the top end portions of the conductors facing each other come in contact with each other along their respective curved surfaces, wherein one of the oppositely facing surfaces of the first conductor and the second conductor is formed with a recess portion extending along the inclined surface of the instant conductor, and the other surface is formed with a projection portion extending along the inclined surface of the instant conductor, and the recess portion and the projection portion face each other in the axial directions of the conductors to grip a biotissue therebetween, and wherein said medical treatment instrument further comprising a conductive outer conductor electrically connectable to a ground of a high-frequency power source, and coating the outside of the first conductor via an insulating layer, and arranged coaxially of the first conductor, wherein the second conductor is relatively shiftable in its axial direction with respect to the outer conductor while being in contact with the outer peripheral portion of the outer conductor.

2. A medical treatment instrument according to claim 1, further comprising a conductive connecting member for connecting the outer conductor with the second conductor in a relative shiftable manner, wherein the connecting member comes to the vicinity of a top end portion of the outer conductor such that when the outer conductor and the second conductor are relatively shifted at least the top end portions of the first conductor and the second conductor slide against the biotissue.

3. A medical treatment instrument according to claim 1, wherein one of the oppositely facing surfaces of the first conductor and the second conductor is formed with a recess portion extending along the inclined surface of the instant conductor, and the other surface is formed with a projection portion extending along the inclined surface of the instant conductor, and the recess portion and the projection portion face each other in the axial directions of the conductors to grip a biotissue therebetween.

4. A medical treatment instrument according to claim 1, further comprising a conductive outer conductor electrically connectable to a ground of a high-frequency power source, and coating the outside of the first conductor via an insulating layer, and arranged coaxially of the first conductor, wherein the second conductor is relatively shiftable in its axial direction with respect to the outer conductor while being in contact with the outer peripheral portion of the outer conductor.

5. A medical treatment instrument according to claim 4, further comprising a conductive connecting member for connecting the outer conductor with the second conductor in a relative shiftable manner, wherein the connecting member comes to the vicinity of a top end portion of the outer conductor such that when the outer conductor and the second conductor are relatively shifted in such a manner that at least the top end portions of the first conductor and the second conductor slide against the biotissue.

6. A medical treatment apparatus comprising a medical treatment instrument including a first conductor and a second conductor extending in parallel directions to each other and relatively shiftable in their axial directions, each conductor comprising an electrode located at a top portion of the conductor, and a high-frequency voltage being applied to the top end portions of the conductors so as to coagulate and cut a biotissue held between a top end portion of the first conductor and a top end portion of the second conductor, the top end portion of the first conductor and the top end portion of the second conductor being inclined in the same direction with respect to the axial directions of the both conductors, and the relative shift of the conductors in their axial directions allowing the top end portions of the both conductors to come close to each other to grip the biotissue therebetween, and when the conductors are further relatively shifted in their axial direction the top end portions of the conductors grip the biotissue, and slide against the biotissue in the same direction and the electrodes generate a frictional force to cut the biotissue, the medical treatment instrument being connectable with a high-frequency power source capable of supplying microwave electric power, the high-frequency power source applying a microwave voltage to the top end portion of the first conductor and the top end portion of the second conductor so that the biotissue held between the top end portions of the conductors is fixed, coagulated, and then cut, wherein the top end portion of the first conductor and the top end portion of the second conductor are curved in the same direction with respect to the axial directions of the conductors and having curvature radii of the top end portion of the first conductor and the top end portion of the second conductor that are different and are set in such a manner that, when the conductors are relatively shifted in the axial directions, the curved surfaces of the top end portions of the conductors facing each other come in contact with each other along their respective curved surfaces, wherein one of the oppositely facing surfaces of the first conductor and the second conductor is formed with a recess portion extending along the inclined surface of the instant conductor, and the other surface is formed with a projection portion extending along the inclined surface of the instant conductor, and the recess portion and the projection portion face each other in the axial directions of the conductors to grip a biotissue therebetween, and said medical treatment apparatus further comprising a conductive outer conductor electrically connectable to a ground of a high-frequency power source, and coating the outside of the first conductor via an insulating layer, and arranged coaxially of the first conductor, wherein the second conductor is relatively shiftable in its axial direction with respect to the outer conductor while being in contact with the outer peripheral portion of the outer conductor.

7. A medical treatment apparatus according to claim 6, further comprising a conductive connecting member for connecting the outer conductor with the second conductor in a relative shiftable manner, wherein the connecting member comes to the vicinity of a top end portion of the outer conductor such that when the outer conductor and the second conductor are relatively shifted in such a manner that at least the top end portions of the first conductor and the second conductor slide against the biotissue.

8. A medical treatment apparatus according to claim 6, wherein one of the oppositely facing surfaces of the first conductor and the second conductor is formed with a recess portion extending along the inclined surface of the instant conductor, and the other surface is formed with a projection portion extending along the inclined surface of the instant conductor, and the recess portion and the projection portion face each other in the axial directions of the conductors to grip a biotissue therebetween.

9. A medical treatment apparatus according to claim 6, further comprising a conductive outer conductor electrically connectable to a ground of a high-frequency power source, and coating the outside of the first conductor via an insulating layer, and arranged coaxially of the first conductor, wherein the second conductor is relatively shiftable in its axial direction with respect to the outer conductor while being in contact with the outer peripheral portion of the outer conductor.

10. A medical treatment apparatus according to claim 9, further comprising a conductive connecting member for connecting the outer conductor with the second conductor in a relative shiftable manner, wherein the connecting member comes to the vicinity of a top end portion of the outer conductor such that when the outer conductor and the second conductor are relatively shifted in such a manner that at least the top end portions of the first conductor and the second conductor slide against the biotissue.

* * * * *